Figure 1:
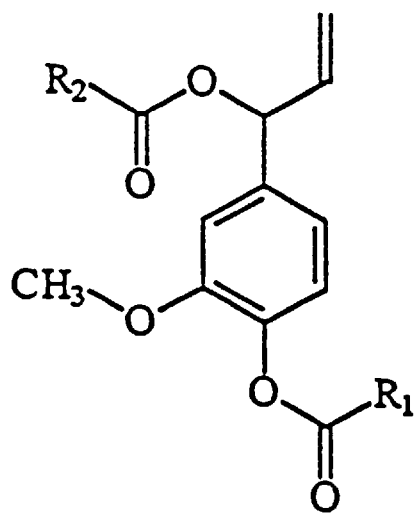
Figure 2:
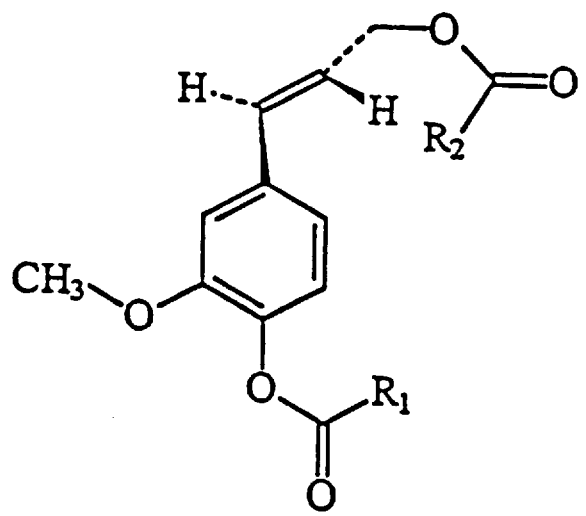
Figure 3:
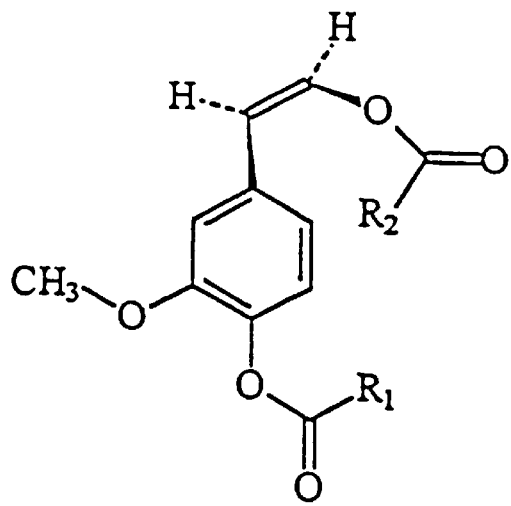
Figure 4:
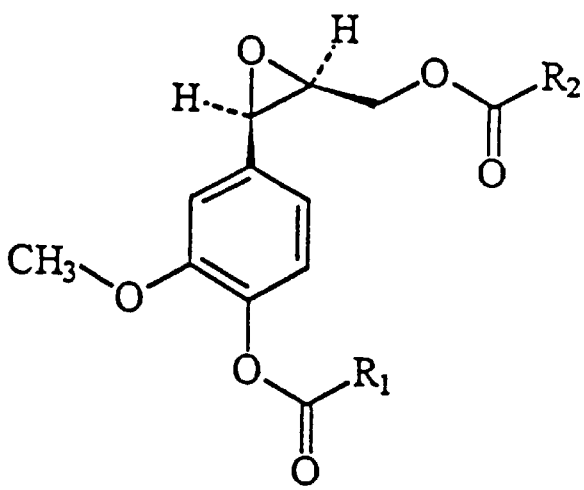
Figure 5:
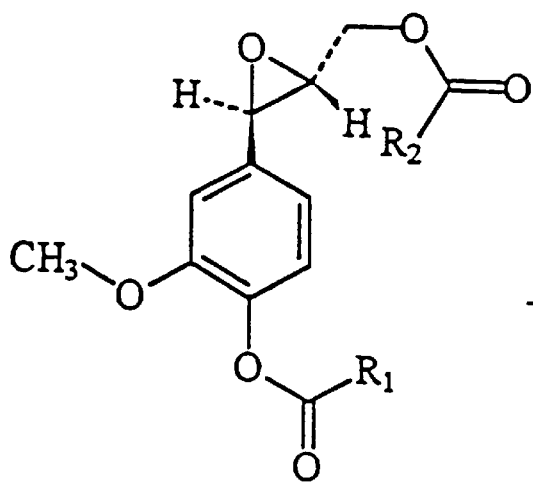

United States Patent
Reichling et al.

Patent Number: 5,811,458
Date of Patent: Sep. 22, 1998

[54] PHENYL PROPANE DERIVATIVES AS ANTIBIOTICS AND LIPOXYGENASE INHIBITORS

[76] Inventors: Jurgen Reichling, Keplerstrasse 33, DE-69207 Sandhausen; Volker Hingst, Am Kastanienberg 8, DE-69151 Neckargemund; Ulla Ohlenmacher, Am Heiligenhaus 13, DE-69126 Heidelberg, all of Germany

[21] Appl. No.: 637,825

[22] PCT Filed: Nov. 11, 1994

[86] PCT No.: PCT/DE94/01333

§ 371 Date: Jul. 30, 1996

§ 102(e) Date: Jul. 30, 1996

[87] PCT Pub. No.: WO95/13263

PCT Pub. Date: May 18, 1995

[30] Foreign Application Priority Data

Nov. 12, 1993 [DE] Germany .................. 43 38 796.9

[51] Int. Cl.⁶ ................................................ A61K 31/235
[52] U.S. Cl. ..................... 514/548; 560/144; 514/475; 514/546; 549/549
[58] Field of Search .................. 560/144; 514/546, 514/475, 548; 549/549

[56] References Cited

U.S. PATENT DOCUMENTS

| | | | |
|---|---|---|---|
| 4,533,746 | 8/1985 | Wilson et al. | 560/144 |
| 5,283,352 | 2/1994 | Backstrom et al. | 560/144 |

OTHER PUBLICATIONS

Mitsui et al, Chem. Abst, vol. 86, #106, 806 h (1977).

*Primary Examiner*—James H. Reamer
*Attorney, Agent, or Firm*—Barnes & Thornburg

[57] ABSTRACT

The invention relates to phenyl propane derivatives of the general formulae:

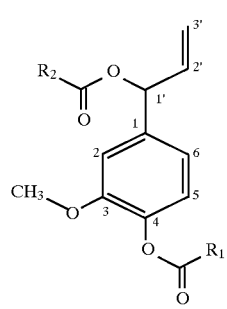

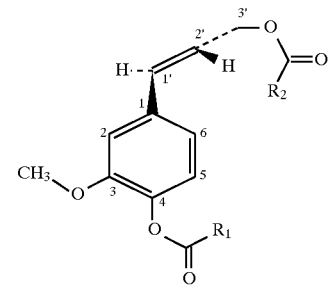

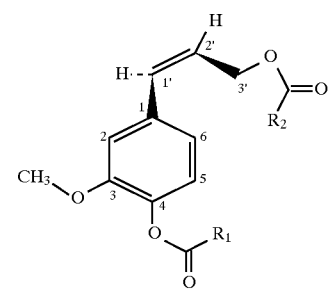

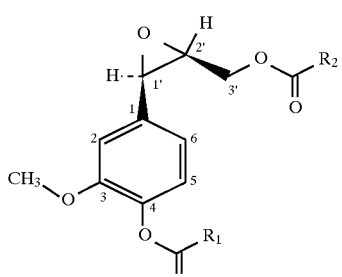

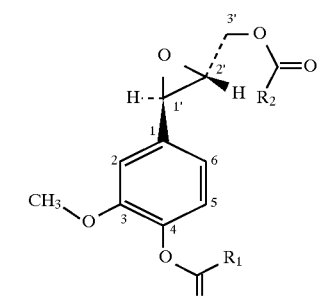

or their mixtures, in which $R_1$ and $R_2$ are a branched or straight-chained alkyl residue of the general formula $C_nH_{2n+1}$ with n=1–18, for use as a therapeutic agent.

5 Claims, 2 Drawing Sheets

PHENYL PROPANE DERIVATIVES AS ANTIBIOTICS AND LIPOXYGENASE INHIBITORS

In recent times the use of natural materials in medicine has become increasingly important. Such analogue natural materials must however be simple and cost-effective to produce, and their therapeutic action must at least approximate to or even entirely equate to that of synthetically-produced preparations. Until now, these requirements have been satisfied by very few natural preparations.

Proceeding from this basis it is the object of the present invention to propose therapeutic active ingredients which are derived from natural materials, these analogue natural materials having to be capable of manufacture by simple and cost-effective methods. The therapeutic action is to correspond approximately to that of synthetic preparations.

This object is achieved by the phenyl propane derivatives defined in more detail in Patent claim 1. Patent claims 4 to 6 show preferred uses of the phenyl propane derivates, while Patent claims 6 and 7 feature the use of the phenyl propane derivates as medicine.

Surprisingly, it has become apparent that the phenyl propane derivates (phenyl proponoids) contained in coreopsis types (asteraceae), with their unusual structural features, are outstandingly suitable as a therapeutic active ingredient, particularly as an antibacterial agent. The phenyl propane derivates according to the invention are diesters of 1'-hydroxyeugenol or diesters of (epoxy)-E/Z-coniferyl alcohols. The occurrence of the diesters of 1'-hydroxyeugenol and of the epoxy-Z coniferyl alcohol (natural substances) appears to be largely restricted to the species coreopsis. Until now only the diacetate of 1'-hydroxyeugenol has been found outwith the species coreopsis in alpinia galanga (zingiberaceae).

It is particularly preferred if the alkyl residue R1 or R2 of the ester group is either methyl, isopropyl, 1-methylpropyl or isobutyl. Quite particularly preferred are the phenyl propane derivates with R1 isopropyl and R2 methyl, isopropyl, 1-methylpropyl or isobutyl.

The phenyl propane derivates described above have surprisingly proved to be extensively selectively-acting antibacterial materials. They are capable of selectively combating problem germs such for example as staph. epidermidis, staph. haemolyticus, or acinetobacter calcoaceticus. In this respect it has become apparent that the antibacterial effect is in part better than for example that of the known antibiotic Cefuroxim®.

Apart from this use as antibiotics, the abovenamed, more extensively described phenyl propane derivates are also suitable for inhibiting the activity of 5-lipoxygenase in human leucocytes. That is, 5-lipoxygenase catalyses the first two reaction stages of the conversion of arachidonic acid to the biologically highly-active leucotrienes $B_4$, $C_4$, $D_4$ and $E_4$. Leucotrienes are important mediators in infective and allergenic reactions. There is therefore great interest in developing corresponding inhibitors which suppress the activity of 5-lipoxygenase. It is now surprisingly revealed that the phenyl propane derivates described above are also suitable for inhibition of the 5-lipoxygenase activity in basophile leukaemia cells of the rat, and in human leucocytes.

Accordingly, by means of the phenyl propane derivates proposed according to the invention, there is proposed a new therapeutic active ingredient with interesting properties in various fields of application.

The phenyl propane derivates may thus be used in medicines with carrier, additive and accessory agents known per se.

The phenyl propane derivates according to the invention may in this case preferably be applied percutaneously, per orem or rectally. A further field of application is the coating of catheters.

In the case of percutaneous application, the phenyl propane derivates are preferably used in the form of powders, ointments, solutions or occlusion dressings. This is advantageous as, after penetration of the skin (hair follicles, injuries) or of the mucous membrane, staphylococci show a tendency to remain at the locus of penetration, causing local infections involving the formation of pus.

For per-orem or rectal application, suitable uses are in the form of pills, tablets, capsules, solutions, emulsions, suppositories, rectal capsules or microclysms. This form of application is particularly suitable in an ulcerous staphylococcal endocarditis which frequently occurs after heart operations.

A factor to be specially emphasised in the phenyl propane derivates according to the invention is their high degree of effectiveness against coagulase-negative staphylococci. These have the capacity to adhere to plastics (e.g. catheters), and there to multiply. Thus they can be washed into the bloodstream and cause sepsis-type syndromes. Coating of catheters, for example with 1'-hydroxyeugenol derivatives, is advantageous as prophylaxis of such complications. Chemical bonding of the molecules to the surface of the plastics is possible with almost no loss of effectiveness. Adhesion to the catheter may also be carried out, as the intensely lipohilic substances have no affinity with the mostly hydrophilic body fluids.

A particularly advantageous factor in the phenyl propane derivatives proposed according to the invention is that they are simple and cost-effective to manufacture. A prescription for synthesis of the phenyl propane derivatives according to the invention is for example indicated in Z. Naturforsch. 44C, 7–11 (1989). Further sources are cited in this publication, in which further such derivates and corresponding manufacturing instructions are described.

The invention will be described in more detail in the following with reference to the use of phenyl propane derivates as a selective antibacterial agent. The invention may best be understood by referring to the following detailed description and accompanying FIGS. 1–5 which illustrate the invention.

The only material which has until now become known from the literature relates to the utilisation of eugenols, i.e. compounds structurally different from the proposed diesters of 1-hydroxyeugenol and (epoxy)-E/Z-coniferyl alcohols, in conjunction with other agents, as an antiseptic or antibacterial agent.

Thus for example it is proposed in U.S. Pat. No. 3,219, 526 to use eugenol in combination with NMSE (5-nitro-2-methylfurfuryl ether). Particular reference is there made to the fact that, clearly due to the combination of these two active ingredients, a special effect is achieved in relation to the antiseptic action. Other proposals relating to the use of eugenols as an antibacterial and antiseptic agent arise from other combinations with other active ingredients. Thus for example, in DE 39 08 527 a disinfectant is also described, which contains eugenol and other active ingredients.

It was therefore totally surprising and unexpected that the phenyl propane derivates according to the invention should on their own have such surprising properties as regards their antibacterial activity.

The phenyl propane derivates given in FIG. 1 are particularly suitable as an antibacterial agent.

As a test of their antibacterial effect, agar plates with a diameter of 10 cm were used, each plate being provided with 10 ml of agar (Caso-Agar or Müller-Hinton agar). The various bacterial suspensions were respectively applied to $10^6$ KBE per ml of nutrient solution. Of this, 0.3 µl in each case were applied by multipoint inoculator to the agar plates. Parent solutions of various phenyl propane derivates were produced in dichloromethane. Aliquot portions were then removed from the parent solutions, the solvent blown under $N_2$ and dissolved in 100 µl (1%) DMSO. The DMSO solution was then added to 10 ml of liquid agar. 1 mM of substance corresponded to approximately 3–4 mg of substance per agar plate. Growth of the bacteria was inhibited only after addition of 7 DMSO. The minimum inhibiting concentration (MHK) was determined, i.e. the lowest concentration of the substance which inhibited the bacterial growth (macroscopically, no further growth could be detected).

In a widely-applied screening, firstly the phenyl propane derivates of the general formula I with $R_1$ with isopropyl and $R_2$ methyl, isopropyl, isobutyl and 1-methylpropyl were tested in comparison to eugenol and phenol for their bacteriostatic power (see Tables 1 and 2). The eugenol derivate with $R_2$ methyl is entered in Tables 1 and 2 as Eu2, that with $R_2$ isopropyl as Eu3, that with $R_2$ isobutyl as Eu4 and that with $R_2$ 1-methylpropyl as Eu5. Of particular interest is the action of the substances on the staphylococci. Substances Eu2–Eu5 above all proved highly effective against various coagulase-negative staphylococci. Of the 5 coagulase-negative staphylococci, only staph. warneri and staph. simulans were resistant to 1'-hydroxyeugenol derivates. On the other hand, staph. haemolyticus and staph. capitis were extremely well controlled by Eu2–Eu5. The MHK values determined give evidence of outstanding antibacterial action of these substances.

Of interest is the comparison with Cefuroxim, a cephalosporin antibiotic of the second generation (cf. Table 2). In the case of staph. haemolyticus the MHK value for Cefuroxim is above 190 µM, and thus clearly above the MHK values of Eu2–Eu5. Therefore this is the rare case in which a natural vegetable material is clearly more effective in antimicrobial terms than a medically established antibiotic. Racemic compounds were used in the experiments. The optically pure enantiomers however reveal the same effectiveness.

The epoxidised E- and Z-coniferyl alcohol derivates (general formulae IV and V) are just as antibacterially potent as the 1'-hydroxyeugenol derivates (cf. Tables 3 and 4). In this case Z-Co1epox identifies the epoxidised Z-coniferyl alcohol with $R_2$ methyl, and correspondingly for $R_2$ isopropyl (Z-Co2epox) and for $R_2$ isobutyl (Z-Co3epox). The E-coniferyl alcohol derivates are correspondingly identified. Interestingly, they also revealed the same qualitative profile of effectiveness, i.e. they were antimicrobially effective against the same bacteria. They were more effective with staph. aureus, and controlled the coagulase-negative staphylococci just as well as the 1'-hydroxyeugenol derivates.

TABLE 1

Determination of MHK by Agar Dilution in mM

| Substance | Eu2 | Eu3 | Eu4 | Eu5 | Eugenol | Phenol |
|---|---|---|---|---|---|---|
| *Acinet. calcoac.* | <0.75 | <0.75 | 12 | >12 | 2 | 11 |
| *Bac. cereus* ATCC 4342 | <0.75 | 1.5 | >12 | >12 | 2 | 15 |
| *B. subtilis* ATCC 6659 | <0.75 | >12 | >12 | >12 | 3 | 14 |
| *Coryn. dipht.* ATCC 10648 | 3 | 12 | >12 | >12 | 2 | 10 |
| *E. coli* CL | >12 | >12 | >12 | >12 | 4 | 16 |
| *E. coli* ATCC 43822 | >12 | >12 | >12 | >12 | 4 | 18 |
| *E. coli* NCTC 8196 | >12 | >12 | >12 | >12 | 4 | 18 |
| *Klebs. pneu.* ATCC 4356 | >12 | >12 | >12 | >12 | 3 | 18 |
| *Microc. luteus* | >12 | >12 | >12 | >12 | 3 | 10 |
| *Ps. aerug.* CL | >12 | >12 | >12 | >12 | 7 | 10 |
| *Ps. aerug.* ATCC 15442 | >12 | >12 | >12 | >12 | 7 | 10 |
| *Ps. diminuta* ATCC 19146 | >12 | >12 | >12 | >12 | 2 | 10 |
| *Ps. maltophilla* | >12 | >12 | >12 | >12 | 3 | 10 |
| *Sarcina lutea* ATCC 9341 | 3 | 1.5 | 12 | 12 | 4 | 25 |
| *Serratia marcescens* | >12 | >12 | >12 | >12 | 4 | 12 |
| *Shig. flexneri* CL | >12 | >12 | >12 | >12 | 3 | 12 |
| *Shig. flexneri* ATCC 25929 | >12 | >12 | >12 | >12 | 3 | 11 |
| *Salm. typhi* ATCC 6599 | >12 | >12 | >12 | >12 | 3 | 12 |
| *Salm. typhimurium* ATCC 13311 | >12 | >12 | >12 | >12 | 4 | 19 |
| *Staph. aureus* CL | <0.75 | <0.75 | 12 | >12 | 4 | 21 |
| *Staph. aureus* clp 53154 | <0.75 | <0.75 | 6 | >12 | 4 | 24 |
| *Staph. aureus* 6538 Kiel | <0.75 | <0.75 | 12 | >12 | 3 | 19 |
| *Staph. aureus* NCTC 4163 | <0.75 | <0.75 | 12 | >12 | 4 | 19 |
| *Strep. faeclum* DSG 8582 | >12 | >12 | >12 | >12 | 3 | >25 |
| *Strep. faeclum* clp 5855 | >12 | >12 | >12 | >12 | 4 | >25 |
| *Strep. faecalis* ATCC 6057 | 12 | 12 | >12 | >12 | 3 | >25 |
| *Xantho. maltophil.* | >12 | >12 | >12 | >12 | 3 | 10 |
| Strep. with alpha haemolysis | 12 | 12 | >12 | >12 | 3 | 21 |
| Strep. pyo Gr. A beta haemolysis | 6 | 12 | >12 | >12 | 2 | 17 |
| Strep. with beta haemolysis | 6 | 12 | >12 | >12 | 2 | 21 |
| Enterococci with gamma haeomolysis | >12 | >12 | >12 | >12 | / | / |

TABLE 2

Determination of MHK by Agar Dilution

| | Isolated from: | Eu2 MHK in uM | Eu3 MHK in uM | Eu4 MHK in uM | Eu5 MHK in uM | Cefuroxim MHK in uM |
|---|---|---|---|---|---|---|
| *Staph. warneri* | blood culture | >3000 | >3000 | >3000 | >3000 | 1 |
| *Staph. epidermidis* | blood culture | 94 | 47 | 375 | 23 | 6 |
| *Staph. epidermidis* | blood culture | 94 | 47 | 375 | 23 | 6 |
| *Staph. epidermidis* | blood culture | 188 | 188 | 1500 | 188 | 0.4 |
| *Staph. epidermidis* | blood culture | 188 | 188 | 1500 | 188 | 1 |
| *Staph. simulans* | A5689 | >3000 | >3000 | >3000 | >300 | 6 |
| *Staph. epidermidis* | catheter tip | 188 | 47 | 750 | 23 | 1 |
| *Staph. epidermidis* | skin | 188 | 47 | 750 | 47 | 1 |
| *Staph. haemolyt.* | skin | 47 | 23 | 47 | 12 | >190 |
| *Staph. capitis* | blood culture | 375 | 188 | 3000 | >3000 | 0.4 |
| *Staph. epidermidis* | catheter tip | 188 | 94 | 375 | 47 | 1 |
| *Staph. epidermidis* | 3-way tap | 188 | 94 | 3000 | 94 | 1 |
| *Staph. epidermidis* | catheter tip | 188 | 94 | 188 | 23 | 6 |
| *Staph. haemolyt.* | catheter tip | 188 | 94 | 188 | 47 | >190 |
| *Staph. epidermidis* | skin | 188 | 47 | 188 | 23 | 1 |
| *Staph. haemolyt.* | catheter tip | 188 | 23 | 47 | 23 | >190 |
| *Staph. aureus* | throat | 375 | 188 | >3000 | >3000 | 6 |
| *Staph. aureus* | trachea | 750 | 750 | >3000 | >3000 | 6 |
| *Staph. aureus* | wound | 375 | 188 | 3000 | >3000 | 6 |
| *Staph. aureus* | pus | 375 | 188 | >3000 | >3000 | 6 |
| *Staph. aureus* | operation scar | 375 | 188 | >3000 | >3000 | 3 |
| *Staph. aureus* | pleura | 750 | 375 | >3000 | >3000 | 6 |
| *Staph. aureus* | skin | 750 | 188 | >3000 | >3000 | 6 |
| *Staph. aureus* | ear | 750 | 750 | >3000 | >3000 | 3 |
| *Staph. aureus* | trachea | 750 | 750 | >3000 | >3000 | 3 |
| *Staph. aureus* | conjuctiva | 375 | 188 | >3000 | >3000 | 3 |
| *Staph. aureus* | throat | 188 | 188 | 3000 | >3000 | 6 |
| *Staph. aureus* | amputation wound | 188 | 94 | 3000 | >3000 | 3 |
| *Staph. aureus* | ulcus | 375 | 375 | >3000 | >3000 | 3 |
| *Staph. aureus* | throat | 750 | 375 | >3000 | >3000 | 3 |
| *Staph. aureus* | eye | 188 | 94 | 3000 | >3000 | 6 |
| *Staph. aureus* | trachea | 375 | 188 | 3000 | >3000 | 6 |
| *Staph. aureus* | conjunctiva | 375 | 375 | >3000 | >3000 | 6 |
| *Staph. aureus* 6538 Kiel | | 375 | 188 | 12000 | >12000 | 3 |
| *Staph. aureus* NCTC 4163 | | 750 | 375 | 12000 | >12000 | 6 |
| *Staph. aureus* clp 53154 | | 375 | 94 | 6000 | >12000 | 3 |

TABLE 3

Determination of MHK by Agar Dilution

| Substance | Z-Co 1 pox MHK in uM | E-Co 1 epox MHK in uM | Z-Co2epox MHK in uM | E-Co2epox MHK in uM | Z-Co3epox MHK in uM | E-Co3epox MHK in uM |
|---|---|---|---|---|---|---|
| *Acinet. calcoac.* | 375 | 375 | 3000 | 188 | 3000 | 6000 |
| *Bac. cereus* ATCC 4342 | 1500 | 188 | >6000 | <94 | >6000 | 188 |
| *B. subtilis* ATCC 6659 | 1500 | 188 | 1500 | <94 | 750 | 188 |
| *Coryn. dipht.* ATCC 10648 | >6000 | >6000 | >6000 | >6000 | >6000 | >6000 |
| *E. coli* CL | >6000 | >6000 | >6000 | >6000 | >6000 | >6000 |
| *E. coli* ATCC 43822 | >6000 | >6000 | >6000 | >6000 | >6000 | >6000 |
| *E. coli* NCTC 8196 | >6000 | >6000 | >6000 | >6000 | >6000 | >6000 |
| *Klebs. pneu.* ATCC 4356 | >6000 | >6000 | >6000 | >6000 | >6000 | >6000 |
| *Micrococ. luteus* | >6000 | >6000 | >6000 | >6000 | >6000 | >6000 |
| *Ps. aerug.* CL | >6000 | >6000 | >6000 | >6000 | >6000 | >6000 |
| *Ps. aerug.* ATCC 15442 | >6000 | >6000 | >6000 | >6000 | >6000 | >6000 |
| *Ps. diminuta* ATCC 19146 | 1500 | 3000 | >6000 | >6000 | >6000 | >6000 |
| *Ps. maltophilla* | >6000 | >6000 | >6000 | >6000 | >6000 | >6000 |
| *Sarcina lutea* ATCC 9341 | 1500 | 6000 | <94 | 750 | <94 | <94 |
| *Serratia marescens* | >6000 | >6000 | >6000 | >6000 | >6000 | >6000 |
| *Shig. flexneri* Cl | >6000 | >6000 | >6000 | >6000 | >6000 | >6000 |
| *Shig. flexneri* ATCC 25929 | >6000 | >6000 | >6000 | >6000 | >6000 | >6000 |
| *Salm. typhi* ATCC 6599 | >6000 | >6000 | >6000 | >6000 | >6000 | >6000 |
| *Salm. typhimurium* ATCC 13311 | >6000 | >6000 | >6000 | >6000 | >6000 | >6000 |
| *Staph. aureus* CL | <94 | <94 | <94 | <94 | <94 | <94 |
| *Staph. aureus* clp 53154 | 94 | 47 | 94 | 94 | 94 | 47 |
| *Staph. aureus* 6538 Kiel | 94 | 47 | 94 | 94 | <47 | 47 |
| *Staph. aureus* NCTC 4163 | 188 | 94 | 188 | 94 | 94 | 47 |
| *Staph. warneri* Nr. 16 | >6000 | >6000 | >6000 | >6000 | >6000 | >6000 |
| *Staph. epidermidis* Nr. 17 | 188 | 94 | 188 | 94 | 94 | 94 |
| *Staph. simulans* Nr. 173 | >6000 | >6000 | >6000 | >6000 | >6000 | >6000 |
| *Staph. epidermidis* Nr. 187 | 188 | 94 | 188 | 94 | 94 | 94 |

TABLE 3-continued

Determination of MHK by Agar Dilution

| Substance | Z-Co 1 pox MHK in uM | E-Co 1 epox MHK in uM | Z-Co2epox MHK in uM | E-Co2epox MHK in uM | Z-Co3epox MHK in uM | E-Co3epox MHK in uM |
|---|---|---|---|---|---|---|
| *Staph. haemolyt.* Nr. 236 | 94 | 47 | 94 | 94 | <47 | 23 |
| *Strep. faeclum* DSG 8582 | >6000 | >6000 | >6000 | >6000 | >6000 | >6000 |
| *Strep. faeclum* clp 5855 | >6000 | >6000 | >6000 | >6000 | >6000 | >6000 |
| *Strep. faecalis* ATCC 6057 | >6000 | >6000 | >6000 | >6000 | >6000 | >6000 |
| *Xantho. maltophil.* | >6000 | >6000 | >6000 | >6000 | >6000 | >6000 |
| Strep. with alpha haeomolysis | 6000 | 1500 | 6000 | 1500 | 3000 | 3000 |
| Strep. Gr. A | >6000 | >6000 | >6000 | >6000 | >6000 | >6000 |
| Strep. with beta haemolysis | >6000 | >6000 | >6000 | >6000 | >6000 | >6000 |
| Enterococci with gamma haemol. | >6000 | >6000 | >6000 | >6000 | >6000 | >6000 |

TABLE 4

Determination of MHK by Agar Dilution

| Substance | | ZCo1epox MHK in uM | ECo1epox MHK in uM | ZCo2epox MHK in uM | ECo2epox MHK in uM | ZCo3epox MHK in uM | ECo3epox MHK in uM | Cefuroxim MHK in uM |
|---|---|---|---|---|---|---|---|---|
| *Staph. warneri* | blood culture | >375 | >375 | >375 | 375 | 94 | 94 | 1 |
| *Staph. epidermidis* | blood culture | 188 | 188 | 188 | 188 | 188 | 94 | 6 |
| *Staph. epidermidis* | blood culture | 375 | 375 | 188 | 188 | 94 | 94 | 6 |
| *Staph. epidermidis* | blood culture | 375 | 375 | 375 | 375 | 188 | 188 | 0.4 |
| *Staph. epidermidis* | blood culture | 375 | 375 | 375 | 375 | 188 | 188 | 1 |
| *Staph. simulans* | A5689 | >375 | >375 | >375 | >375 | 188 | >375 | 6 |
| *Staph. epidermidis* | trachea | 375 | 375 | 188 | 375 | 188 | 188 | 1 |
| *Staph. epidermidis* | skin | 188 | 188 | 188 | 375 | 94 | 94 | 1 |
| *Staph. haemolyt.* | skin | 47 | 23 | 47 | 23 | 47 | 12 | >190 |
| *Staph. capitis* | blood culture | 188 | 94 | 188 | 94 | 47 | 23 | 0.4 |
| *Staph. epidermidis* | catheter tip | 375 | 375 | 375 | 375 | 188 | 188 | 1 |
| *Staph. epidermidis* | 3-way tap | 375 | 375 | 375 | 375 | 188 | 188 | 1 |
| *Staph. epidermidis* | catheter tip | 188 | 188 | 188 | 188 | 94 | 94 | 6 |
| *Staph. haemolyt.* | catheter tip | 94 | 47 | 188 | 94 | 47 | 23 | 190 |
| *Staph. epidermidis* | skin | 375 | 375 | 188 | 375 | 188 | 188 | 1 |
| *Staph. haemolyt.* | catheter tip | 188 | 47 | 94 | 94 | 47 | 47 | >190 |
| *Staph. aureus* | throat | 375 | 94 | 375 | 188 | 94 | 94 | 6 |
| *Staph. aureus* | trachea | >375 | 94 | >375 | 188 | 188 | 94 | 6 |
| *Staph. aureus* | wounds | 375 | 47 | 375 | 94 | 188 | 47 | 6 |
| *Staph. aureus* | pus | 375 | 188 | 375 | 188 | 188 | 94 | 6 |
| *Staph. aureus* | operation scar | 375 | 188 | 188 | 188 | 188 | 188 | 3 |
| *Staph. aureus* | pleura | >375 | 188 | 375 | 375 | 188 | 94 | 6 |
| *Staph. aureus* | skin | >375 | 188 | >375 | 375 | 94 | 188 | 6 |
| *Staph. aureus* | ear | >375 | 94 | 375 | 94 | 94 | 47 | 3 |
| *Staph. aureus* | trachea | >375 | 94 | >375 | 375 | 188 | 188 | 3 |
| *Staph. aureus* | conjunctiva | >375 | 94 | 375 | 188 | 188 | 94 | 3 |
| *Staph. aureus* | throat | 375 | 188 | 375 | 188 | 188 | 94 | 6 |
| *Staph. aureus* | amputation wound | 375 | 47 | 375 | 188 | 188 | 47 | 3 |
| *Staph. aureus* | ulcus | >375 | 94 | 375 | 375 | 188 | 94 | 3 |
| *Staph. aureus* | throat | >375 | 47 | >375 | 188 | 188 | 188 | 3 |
| *Staph. aureus* | eye | >375 | 47 | 375 | 94 | 94 | 47 | 6 |
| *Staph. aureus* | trachea | 375 | 94 | 375 | 188 | 94 | 94 | 6 |
| *Staph. aureus* | conjunctiva | >375 | 94 | 375 | 375 | 94 | 94 | 6 |
| *Staph. aureus* 6538 Kiel | | 188 | 47 | 188 | 47 | 47 | 47 | 3 |
| *Staph. aureus* NCTC 4163 | | 375 | 188 | 375 | 188 | 94 | 47 | 6 |
| *Staph. aureus* clp 53154 | | 188 | 47 | 188 | 94 | 94 | 47 | 3 |

We claim:

1. An agent for combating bacterial infections containing phenyl propane derivatives of the general formulae:

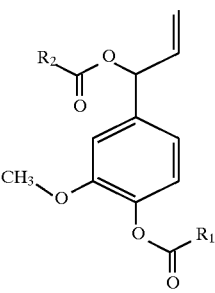

I or

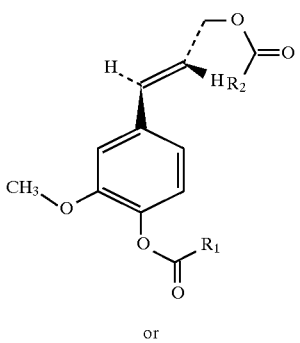

or

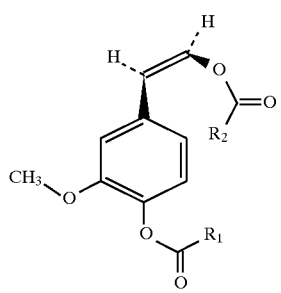

or

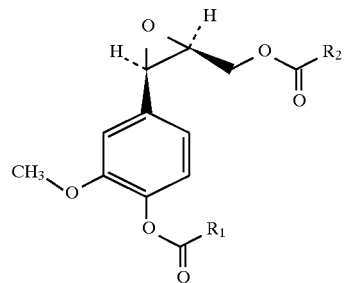

II or

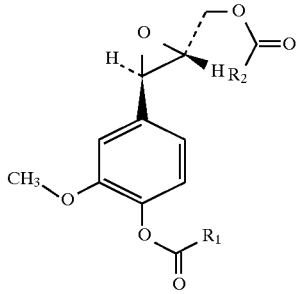

III

IV

V or their mixtures, in which $R_1$ and $R_2$ are independently branched or straight chained alkyl residue of the general formula $C_nH_{2n+1}$ where n is 1–18, with the proviso that, in Formula I, $R_1$ and $R_2$ are not simultaneously $CH_3$, for use as a therapeutic agent.

2. An agent according to claim 1, wherein $R_1$ is methyl, isopropyl or 1-methylpropyl.

3. An agent according to claim 1 wherein $R_1$ and $R_2$ are each independently methyl, isopropyl, isobutyl or 1-methylpropyl.

4. An agent according to claim 1 wherein $R_2$ is methyl, isopropyl, isobutyl or 1-methylpropyl.

5. An agent according to claim 1, 2, 3, or 4 wherein $R_1$ is isopropyl and $R_2$ is methyl, isopropyl, isobutyl or 1-methylpropyl.

* * * * *